US010993620B2

(12) United States Patent
Meyer et al.

(10) Patent No.: US 10,993,620 B2
(45) Date of Patent: May 4, 2021

(54) METHOD FOR LOCATING A FUNCTIONAL BRAIN TISSUE BY ELECTRICAL STIMULATION

(71) Applicant: Carl Zeiss Meditec AG, Jena (DE)

(72) Inventors: Tobias Meyer, Dresden (DE); Martin Oelschlaegel, Dresden (DE); Ute Morgenstern, Dresden (DE); Stephan B. Sobottka, Dresden (DE); Gabriele Schackert, Dresden (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/586,972

(22) Filed: Sep. 28, 2019

(65) Prior Publication Data
US 2020/0100678 A1 Apr. 2, 2020

(30) Foreign Application Priority Data
Sep. 28, 2018 (DE) .................... 10 2018 124 114.3

(51) Int. Cl.
*A61B 5/00* (2006.01)
*A61B 5/0484* (2006.01)
(52) U.S. Cl.
CPC .......... *A61B 5/0042* (2013.01); *A61B 5/0484* (2013.01); *A61B 2560/0238* (2013.01)
(58) Field of Classification Search
CPC ............ A61B 2576/026; A61B 5/0484; A61B 5/4064; A61B 2560/0238; A61B 5/0082; A61B 5/0042
See application file for complete search history.

(56) References Cited

U.S. PATENT DOCUMENTS

| 9,095,255 | B2 | 8/2015 | Fanenbruck |
| 9,801,549 | B2 | 10/2017 | Panitz et al. |
| 2002/0099295 | A1* | 7/2002 | Gil ...................... A61B 5/4064 |
| | | | 600/476 |

OTHER PUBLICATIONS

Oelschlaegel et al. "Intraoperative optical imaging of metabolic changes after a di-rect cortical simulation—a clinical tool for guidance during tumor resection?", (2018), in Biomed. Eng. Biomed. Tech.

(Continued)

*Primary Examiner* — Christine H Matthews
*Assistant Examiner* — Joshua Daryl D Lannu
(74) *Attorney, Agent, or Firm* — Falk Ewers; Ewers IP Law PLLC (57) ABSTRACT

A method for locating a functional brain tissue by electrical stimulation includes performing electrical stimulations of different areas of the brain tissue to activate brain tissue regions identifying the functional brain tissue, recording an image or a video sequence of the brain tissue during and/or after a stimulation, comparing the recorded image or the video sequence with a reference image or a reference video sequence recorded without stimulation to determine a position of the brain tissue region that is activated by the stimulation. At least two stimulations of a plurality of electrical stimulations are performed, one directly after the other or simultaneously, and the recording of an image or a video sequence of the portion of brain tissue takes place during and/or after each performance of one of the at least two stimulations or during and/or after the simultaneous performance of the at least two stimulations.

17 Claims, 5 Drawing Sheets

(56) References Cited

OTHER PUBLICATIONS

Office Action issued in German Patent Application No. DE 10 2018 124 114.3 (from which this application claims priority), dated Aug. 2, 2019 and English language translation thereof.
Decision to Grant issued in German Patent Application No. DE 10 2018 124 114.3 (from which this application claims priority), dated Dec. 23, 2019 and English language translation thereof.

* cited by examiner

METHOD FOR LOCATING A FUNCTIONAL BRAIN TISSUE BY ELECTRICAL STIMULATION

CROSS REFERENCE TO RELATED APPLICATIONS

This application claims priority to German patent application DE 10 2018 124 114.3, filed Sep. 28, 2018, the entire content of which is incorporated herein by reference.

TECHNICAL FIELD

The present disclosure relates a method for locating a functional brain tissue of a portion of a brain tissue by electronic stimulation. In addition, the present disclosure relates to a computer-implemented method for optimizing stimulation locations and a stimulation sequence when performing a plurality of electrical stimulations of different areas of the portion of the brain tissue for activating brain tissue regions. Furthermore, the disclosure relates to a non-transitory computer-readable storage medium with instructions stored thereon for optimizing stimulation locations and a stimulation sequence when performing a plurality of electrical stimulations of different areas of a portion of the brain tissue for activating brain tissue regions as well as an apparatus for locating functional a brain tissue of a portion of a brain tissue.

BACKGROUND

In the course of neurosurgical interventions for the resection of tumor tissue, an aim of the surgeon is complete removal of the malignant tissue while at the same time preserving and specifically sparing healthy, functional tissue. After opening the skull and exposing the surface of the brain, in many cases these different types of tissue are not distinguishable from one another on a purely visual basis in the exposed portion of brain tissue, which makes it more difficult to achieve the stated aims of the intervention. One possibility for assisting the surgeon in distinguishing between the types of tissue is that of combining optical imaging and direct cortical stimulation. In the case of this method, the exposed cortex (a thin layer of nerve cells at the outer periphery of the brain) is electrically stimulated at discrete points with bipolar electrodes. At the same time, the responses to the stimulation in the form of changes in the optical properties of the cortical tissue are recorded, for example with a camera, and evaluated. On the basis of the changes in the optical properties of the cortical tissue thus documented, the functional state and/or the type of tissue in the region of the stimulation is deduced. Methods in which images are recorded before and/or during the stimulation and the functional brain areas are determined by evaluating the images recorded are described for example in Oelschlägel et al. "Intraoperative optical imaging of metabolic changes after a direct cortical stimulation—a clinical tool for guidance during tumor resection?" in Biomed. Eng. Biomed. Tech. 2018, appearing online on Feb. 5, 2018, available at https://doi.org/10.1515/bmt-2017-0156, in U.S. Pat. Nos. 9,095,255 B2 and in 9,801,549 B2.

The procedure described above must be repeated a number of times at different locations in order to document the entire exposed portion of brain tissue, in order in this way to be able to make an all-inclusive statement about the entire exposed portion of brain tissue. In the case of the conventional methods, the stimulations are performed individually and one after the other. For example, it is described in Oelschlägel et al. "Intraoperative optical imaging of metabolic changes after a direct cortical stimulation—a clinical tool for guidance during tumor resection?" in Biomed. Eng. Biomed. Tech. 2018, appearing online on Feb. 5, 2018, available at https://doi.org/10.1515/bmt-2017-0156, that image data of a 30-second rest period, a 5-second stimulation period and an 85-second post-stimulation period are recorded at the stimulation location, which for each stimulation results in a length of the data record of 120 seconds. This procedure is used in practice for example when mapping the voice functionality on a patient when awake. In the case of for example ten different stimulations, this procedure would require a time period of at least 20 minutes. The interrogation process therefore takes several minutes, and when there are many stimulations, there is a risk that the surgeon will lose the overview of the stimulation locations already interrogated. As a result, there is a risk that the entire exposed portion of brain tissue is not examined. Moreover, the long time it takes for the examination due to the stimulations being performed one after the other interrupts the therapeutic intervention, and the result is not necessarily definitive.

SUMMARY

It is an object of the present disclosure to provide a method for locating a functional brain tissue that requires less time than the methods known from the prior art.

A further object of the present disclosure is to provide a computer-implemented method for optimizing the stimulation locations and the stimulation sequence when performing a plurality of electrical stimulations of different areas of a portion of brain tissue for activating brain tissue regions that makes it possible for the stimulation procedure to be performed quickly.

Furthermore, it is an object of the present disclosure to provide a nonvolatile non-transitory computer-readable storage medium with instructions stored thereon, when executed by a processor, to optimize the stimulation locations and the stimulation sequence when performing a number of electrical stimulations of different areas of a portion of tissue for activating brain tissue regions that makes it possible for the stimulation locations and the stimulation sequence to be optimized in such a way that the stimulation procedure can be performed quickly.

Finally, it is an object of the present disclosure to provide a device configured to locate functional brain tissue of a portion of brain tissue by electrical stimulation with which it is possible to perform the stimulation procedure quickly.

The objects are achieved by a method for locating functional brain tissue, by a computer-implemented method, by a nonvolatile non-transitory computer-readable storage medium, as well as by a device configured to locate functional brain tissue as described herein.

A method according to an aspect of the disclosure for locating functional brain tissue of a portion of brain tissue by electrical stimulation includes:
  performing a number of electrical stimulations of different areas of the portion of brain tissue for activating brain tissue regions of the portion of brain tissue, in particular cortical brain tissue regions of the portion of brain tissue, an activated brain tissue region identifying functional brain tissue of the portion of brain tissue;
  recording at least one image or a video sequence of a portion of brain tissue during and/or after a stimulation; and comparing an image recorded during and/or after at least one stimulation or a video sequence recorded during and/or after at least one stimulation with a reference image or a reference video sequence of the portion of brain tissue without stimulation, in order to determine the position of at least one brain tissue region in the portion of brain tissue that is activated in the stimulation.

According to an aspect of the disclosure, at least two stimulations from the number of electrical stimulations are performed one directly after the other or at the same time and the recording of an image or a video sequence of the portion of brain tissue takes place during and/or after each performance of one of the at least two stimulations or during and/or after the simultaneous performance of the at least two stimulations.

In other words, in the course of the method according to the disclosure, a reference image is not recorded before every stimulation, but instead at least two stimulations take place at the same time or one directly after the other, without a reference image being recorded in between. This makes it possible to dispense with the recording of image data of a 30-second rest phase between the two stimulations described by Oelschlägel et al., as a result of which the time period required for performing the stimulation procedure can be reduced.

The time period required for performing the stimulation procedure can be reduced particularly effectively if only a single reference image or a single reference video sequence of the portion of brain tissue is recorded before performing the number of electrical stimulations of different areas of the portion of brain tissue. In particular, there is in this case the possibility that each comparison of an image recorded during and/or after at least one stimulation or of a video sequence recorded during and/or after a stimulation takes place with the same single reference image or the same single reference video sequence. In the example described at the beginning, in which 20 minutes are required for ten stimulation locations, only one reference image would then be needed, so that it would only be necessary for an image of a 30-second rest phase to be recorded once. There is no need for the other 9 reference images, so that 9×30 seconds, that is to say 4.5 minutes, can be saved. Therefore, as compared with the example stated at the beginning with 15.5 minutes, the time required for the stimulation procedure is reduced by almost a quarter.

The method according to an aspect of the disclosure can be made possible in particular by the number of stimulations, the associated stimulation locations in the portion of brain tissue and the sequence of the electrical stimulations being optimized in such a way that the brain tissue regions activated by the different stimulations do not spatially overlap one another and/or activations of the brain tissue regions that are caused by different stimulations and spatially overlap one another do not temporally overlap. The result of the optimization can then be stored and retrieved during the stimulation procedure, in order to perform the stimulation procedure with the optimized number of stimulations, the optimized stimulation locations in the portion of brain tissue and the optimized sequence of the electrical stimulations. The optimization makes it possible to provide a stimulation procedure that can be performed particularly quickly.

The optimizing of the number of stimulations, the associated stimulation locations in the portion of brain tissue, and the sequence of the electrical stimulations may in this case include in particular:

determining an areal extent of the stimulation-activated brain tissue region to be expected in the case of a stimulation of an area of the portion of brain tissue;

determining a number of stimulations required for covering the overall area of the portion of brain tissue and the associated stimulation locations from the overall area of the portion of brain tissue and the determined areal extent to be expected of the activated brain tissue region;

establishing a sequence of the stimulations with the respective stimulation locations in the portion of brain tissue while making allowance for the decay time of an activation of a brain tissue region caused by a stimulation for the determined number of stimulations in such a way that successive stimulation locations are spatially far apart from one another to such an extent that the brain tissue regions activated by the respective stimulation do not overlap one another and/or the stimulations at stimulation locations lying spatially close to one another take place at a time interval of such a length that the activation resulting from the stimulation of one of the stimulation locations lying spatially close to one another has decayed when the stimulation of the other of the stimulation locations lying spatially close to one another takes place.

Typical decay times are in this case 30 to 60 seconds. With the optimization described, consequently, a stimulation sequence in which stimulation locations lying spatially close to one another are used for the stimulation at a greater time interval than stimulation locations spatially far apart from one another is determined. In this case, it is even possible that stimulation locations that are spatially sufficiently far apart from one another are stimulated at the same time if the brain tissue regions activated by the stimulation do not spatially overlap one another. The stimulation at the same time makes possible a further reduction of the time required for performing the stimulation process.

Determining the areal extent of the activated brain tissue region to be expected in the case of a stimulation of an area of the portion of brain tissue may take place for example on the basis of a calibration image recorded during and/or after a stimulation or a calibration video sequence recorded during and/or after a stimulation. The areal activation of the activated brain tissue region may then be determined for example by comparing the calibration image or the calibration video sequence with a reference image or a reference video sequence that shows the brain area without stimulation. Typically, the areal extents of the activated brain tissue regions are largely independent of the stimulation location, so that the number of stimulations required for the stimulation procedure can in the simplest case be determined by dividing the overall area of the portion of brain tissue by the areal extent of the activated brain tissue region. More sophisticated methods may make allowance for maximum distances between the stimulation locations and/or increased minimum distances between the stimulation locations of successive stimulations. Although the maximum distances may possibly have the effect of slightly increasing the number of stimulation locations, and consequently the number of required stimulations, the risk of part of the portion of brain tissue not being covered by the stimulation procedure because of an overestimated areal extent to be expected is reduced. The maximum distances between the individual stimulation locations therefore make it possible to ensure that the entire portion of brain tissue is covered in the stimulation procedure, even if individual activated brain tissue regions have a smaller areal extent than the areal extent to be expected. The increased minimum distances between the stimulation locations of successive stimulations make it possible to avoid an unintended overlap of the brain tissue regions activated by the successive stimulations because of a variance of the areal extent of different activated brain tissue regions.

In the course of the method according to an aspect of the disclosure, while making allowance for the direction in which the recording of the at least one image or the video sequence of the portion of brain tissue takes place during and/or after a stimulation, the position and/or orientation of an electrode used for the stimulation may also be optimized in such a way that coverings of the activated brain tissue region caused by the electrode in the image recorded during and/or after a stimulation or in the video sequence recorded during and/or after a stimulation are minimized. In addition or as an alternative, while making allowance for the direction of illumination, the position and/or orientation of the electrode used for the stimulation may be optimized in such a way that shadows cast in the portion of brain tissue that are caused by the electrode in the image recorded during and/or after a stimulation or in the video sequence recorded during and/or after a stimulation are minimized. By suitable coordination of the direction of illumination and the direction in which the recording of the at least one image or the video sequence takes place, it is possible to achieve a considerable minimization of the shadows cast while at the same time significantly minimizing the coverings.

In the course of the method according to an aspect of the disclosure, for recording an image or a video sequence of the portion of brain tissue during and/or after a stimulation, a single video sequence that documents the entire number of electrical stimulations of different areas of the portion of brain tissue may be recorded, so that the entire stimulation procedure can be reproduced in a single video sequence. If need be, individual images, which show specific activated brain tissue regions, can be extracted from this video sequence.

The computer-implemented method according to an aspect of the disclosure for optimizing the stimulation locations and the stimulation sequence when performing a number of electrical stimulations of different areas of a portion of brain tissue for activating brain tissue regions of the portion of brain tissue includes:
  determining an areal extent of the stimulation-activated brain tissue region to be expected in the case of a stimulation of an area of the portion of brain tissue;
  determining a number of stimulations required for covering the overall area of the portion of brain tissue and the associated stimulation locations from the overall area of the portion of brain tissue and the determined areal extent to be expected of the activated brain tissue region;
  establishing a sequence of the stimulations with the respective stimulation locations in the portion of brain tissue while making allowance for the decay time of an activation of a brain tissue region caused by a stimulation for the determined number of stimulations in such a way that successive stimulation locations are spatially far apart from one another to such an extent that the brain tissue regions activated by the respective stimulation do not overlap one another and/or the stimulations at stimulation locations lying spatially close to one another take place at a time interval of such a length that the activation resulting from the stimulation of one of the stimulation locations lying spatially close to one another has decayed when the stimulation of the other of the stimulation locations lying spatially close to one another takes place.

The computer-implemented method according to an aspect of the disclosure makes it possible to optimize the stimulation sequence for the method for locating functional brain tissue on a computer.

In the computer-implemented method according an aspect of to the disclosure, the areal extent of the activated brain tissue region to be expected in the case of a stimulation of an area of the portion of brain tissue may be determined on the basis of a calibration image recorded during and/or after a stimulation or a calibration video sequence recorded during and/or after a stimulation. Generally, a single stimulation of a single area of the portion of brain tissue, i.e., a single stimulation at a single stimulation location of the portion of brain tissue, is sufficient.

Moreover, the computer-implemented method according to an aspect of the disclosure may be designed in such a way that, while making allowance for the direction in which the recording of the at least one image or the video sequence of the portion of brain tissue takes place during and/or after a stimulation, the position and/or orientation of the electrode used for the stimulation may be optimized in such a way that coverings of the activated brain tissue region caused by the electrode in the image recorded during and/or after a stimulation or in the video sequence recorded during and/or after a stimulation are minimized. In addition or as an alternative, the computer-implemented method according to an aspect of the disclosure may be designed in such a way that, while making allowance for the direction of illumination, the position and/or orientation of the electrode used for the stimulation may be optimized in such a way that shadows cast that are caused by the electrode in the image recorded during and/or after a stimulation or in the video sequence recorded during and/or after a stimulation are minimized.

Wherever further details have been described above in connection with the method according to an aspect of the disclosure for locating functional brain tissue with respect to the optimizing of the number of stimulations, the associated stimulation locations or the sequence of stimulations, these details apply correspondingly to the computer-implemented method according to the disclosure.

According to another aspect of the disclosure, a nonvolatile non-transitory computer-readable storage medium with instructions stored thereon is also provided for optimizing the stimulation locations and the stimulation sequence when performing a number of electrical stimulations of different areas of a portion of brain tissue for activating brain tissue regions of the portion of brain tissue. When the instructions are carried out on a computer, the instructions cause the computer to carry out the following steps:
  determining the areal extent of the stimulation-activated brain tissue region to be expected in the case of a stimulation of an area of the portion of brain tissue;
  determining the number of stimulations required for covering the overall area of the portion of brain tissue and the associated stimulation locations from the overall area of the portion of brain tissue and the determined areal extent to be expected of the activated brain tissue region;
  establishing the sequence of the stimulations with the respective stimulation locations in the portion of brain tissue while making allowance for the decay time of an activation of a brain tissue region caused by a stimulation for the determined number of stimulations in such a way that successive stimulation locations are spatially far apart from one another to such an extent that the brain tissue regions activated by the respective stimulation do not overlap one another and/or the stimulations at stimulation locations lying spatially close to one another in such a way that the brain tissue regions activated in the respective stimulation spatially overlap one another take place at a time interval of such a length that the activation resulting from the stimulation of one of the stimulation locations lying spatially close to one another has decayed when the stimulation of the other of the stimulation locations lying spatially close to one another takes place.

The computer-readable storage medium according to an aspect of the disclosure makes it possible to load the computer-implemented method into a computer for being carried out by the computer.

Statements that have been made with respect to the optimizing of the number of stimulations, the stimulation locations or the stimulation sequence with respect to the method according to an aspect of the disclosure for locating functional brain tissue and/or with respect to the computer-implemented method according to an aspect of the disclosure apply correspondingly to the instructions stored on the non-transitory computer-readable storage medium and to the steps caused by the instructions.

A device according to the disclosure configured to locate functional brain tissue of a portion of brain tissue by electrical stimulation includes:

- at least two stimulation electrodes for stimulating areas of the portion of brain tissue for activating brain tissue regions of the portion of brain tissue, an activated brain tissue region of the portion of brain tissue identifying functional brain tissue of the portion of brain tissue;
- at least one camera for recording at least one reference image or a reference video sequence of the portion of brain tissue without stimulation and at least one image or a video sequence of the portion of brain tissue during and/or after a stimulation; and
- an evaluation device, configured to determine on the basis of the comparison of an image recorded during and/or after at least one stimulation or a video sequence recorded during and/or after at least one stimulation with a reference image or a reference video sequence of the portion of brain tissue without stimulation the position of at least one brain tissue region in the portion of brain tissue that is activated in the case of a stimulation.

According to an aspect of the disclosure, the device includes an optimization device configured to optimize the number of stimulations of the associated stimulation locations and the sequence of the stimulations.

With the aid of the optimization device, it is possible to optimize the stimulation procedure in such a way that the time required for performing the stimulation procedure is minimized. The optimization performed by the optimization device corresponds to the optimization described with respect to the method according to the disclosure for locating functional brain tissue, with respect to the computer-implemented method according to an aspect of the disclosure and with respect to the computer-readable storage medium. Therefore, reference is made to the corresponding passages. In all cases, a further optimization may take place during the performance of the stimulation procedure, for example a recalculation of the number of stimulations and/or the stimulation locations in the portion of brain tissue and/or the sequence of the electrical stimulations then taking place.

In particular, such a recalculation may take place after each stimulation of the stimulation procedure, so that a continual optimization takes place.

A camera integrated in a surgical microscope may serve in particular as the at least one camera for recording at least one reference image or a reference video sequence of the portion of brain tissue without stimulation and at least one image or a video sequence of the portion of brain tissue during and/or after a stimulation. Cameras are generally present in any case in modern surgical microscopes, and can be used to perform the method according to an aspect of the disclosure, so that an additional camera is not needed for recording at least one reference image or a reference video sequence of the portion of brain tissue without stimulation and at least one image or a video sequence of the portion of brain tissue during and/or after a stimulation.

BRIEF DESCRIPTION OF THE DRAWINGS

The disclosure will now be described with reference to the drawings wherein.

DESCRIPTION OF EXEMPLARY EMBODIMENTS

Figure 1:
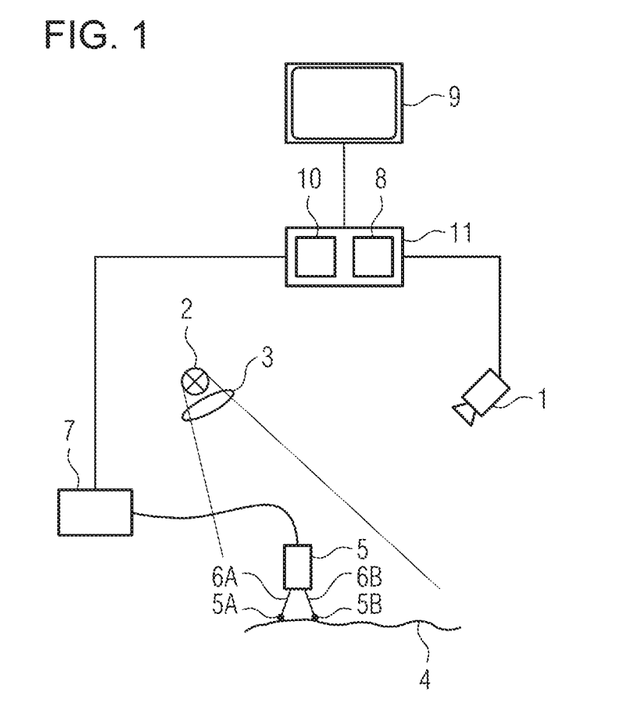
FIG. 1 shows a device for locating functional brain tissue of a portion of brain tissue by electrical stimulation in a schematic diagram.

A device for locating functional brain tissue of an exposed portion of brain tissue by electrical stimulation is explained below with reference to the schematic diagram in FIG. 1. The device includes a recording device for image or video data, which in the present example is formed as a color camera (RGB camera) 1. It may, however, also be formed as a monochrome camera, which is fitted with a spectral filter, which may be configured to allow a narrow wavelength range to pass, for example a range centered around 568 nm, 600 nm or some other wavelength, to pass. When an RGB camera is used, the green channel of the camera may be used for locating functional brain tissue. A camera with a CCD sensor or a camera with a CMOS sensor may be used as the camera 1. The camera 1 may moreover be part of a surgical microscope with which the exposed portion of brain tissue 4 is viewed.

The device additionally includes an illumination device, which in the present example has a halogen lamp 2 as a white light source and an illumination optical device 3 to provide homogeneous illumination of the exposed portion of brain tissue 4 in which functional brain tissue is to be found. The illumination device may also be part of the surgical microscope with which the exposed portion of brain tissue 4 is viewed.

For the stimulation of the brain tissue in the exposed portion of brain tissue 4, a bipolar stimulation electrode 5 is provided. The poles 5A and 5B of the stimulation electrode 5 are respectively located at the end of a flexible portion 6A and 6B, so that the distance between the poles 5A and 5B can be set. The control of the intensity of the current flowing between the poles 5A and 5B and the time for which the current flows are controlled by a stimulation control device 7.

In addition, the device includes an optimization device 8, which serves the purpose of optimizing at least the number of stimulations, the associated stimulation locations in the exposed portion of brain tissue 4 and the sequence of the electrical stimulations. In addition, there is also the possibility that the optimization device 8 determines an optimized stimulation current and/or an optimized stimulation time, which is then output to the stimulation control device 7, which for this purpose is connected to the optimization device 8 for this purpose. The optimization device 8 is additionally connected to the camera 1, in order to receive from the camera 1 image data that are recorded in the course of a calibration measurement.

In order to inform the user, that is to say the treating surgeon, of the stimulation locations determined during the optimization and also the determined stimulation sequence, the optimization device 8 is connected to a monitor 9, or some other display device, on which the stimulation locations and the stimulation sequence are presented. Moreover, at least one of the following items of information may be displayed on the monitor 9: i) the orientation of the stimulation electrode 5 used for the stimulation in the stimulation; ii) the direction from which the stimulation electrode 5 is to be brought up to the respective stimulation location; iii) the intensity of the current that is intended to flow between the poles 5A and 5B during the stimulation; and iv) the duration of current flow during a stimulation.

The device also includes an evaluation device 10, which is connected to the camera and with which functional brain tissue regions can be found in the exposed portion of brain tissue 4 on the basis of video sequences recorded by the camera during the performance of the optimized stimulation procedure. The functional brain tissue regions found are presented on the monitor 9 after completion of the stimulation procedure. In the present exemplary embodiment, the optimization device 8 and the evaluation device 10 take the form of software on a computer 11. Moreover, the stimulation control device 7 may also take the form of software on a computer 11.

The overall device may include individual components, although individual components may also be integrated together in a specific device. Furthermore, there is the possibility of integrating all of the components in a single device. In particular, some or all of the components may be integrated in a surgical microscope. The optimization device 8 and/or the stimulation control device 7 may also be integrated in a computer which is connected to the other components or to the device in which the other components are integrated. For example, the optimization device 8 and the stimulation control device 7 may be integrated in a computer connected to a surgical microscope, the illumination device 2 and 3 and the camera 1 being integrated in the surgical microscope. However, the stimulation electrode 5 is in all cases an independent device, since it must be handled by the surgeon independently of the other components in order to be able to place it at the specified stimulation locations.

Figure 2:
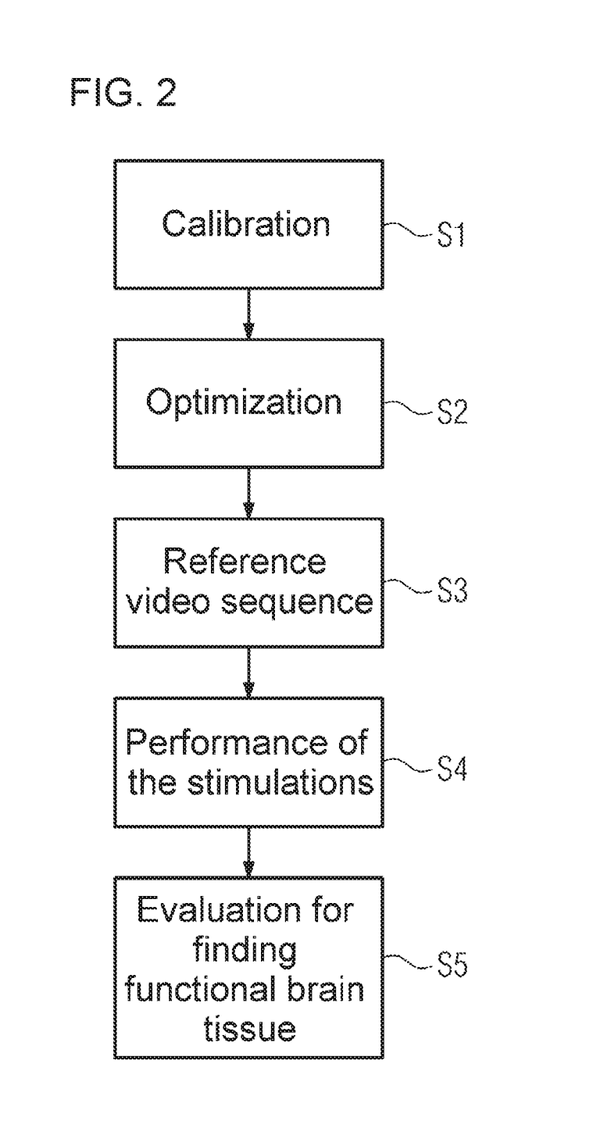
FIG. 2 shows a method for locating functional brain tissue of a portion of brain tissue by electrical stimulation in the form of a block diagram.

The method for locating functional brain tissue is explained in more detail below with reference to FIGS. 2 and 3.

At the beginning of the method, calibrating and data capturing steps may be performed in an optional step S1 if the corresponding data have not already been obtained with the aid of other calibrating and data capturing steps. In the course of the calibrating and data capturing steps, the distance between the poles 5A and 5B of the stimulation electrode 5 and/or the complete geometry of the stimulation electrode 5 as well as the dimensions and the imaging scale of the exposed portion of brain tissue 4 are documented. These data may either be input manually or be captured in an automated manner. Some of these data may for example be taken over from a surgical microscope that is used when performing the surgery. For example, the dimensions of the exposed portion of brain tissue and the imaging scale may be taken over from the surgical microscope if the surgical microscope determines the dimensions of the exposed portion of brain tissue 4 and the imaging scale from the image data obtained.

Moreover, in the course of the calibrating and data capturing steps, the camera 1 records an image of the exposed portion of brain tissue 4 in which for example important anatomical regions, for instance individual gyri (gyms: one of the convolutions of the brain protruding from the brain mass) and/or anatomical landmarks, for example sulci (fissures), vessels, etc., are segmented, for example with the aid of image processing software. MRT data (MRT: magnetic resonance tomography), CT data (CT: computed tomography), internal image features, which are determined on the basis of the image recorded, or manually performed segmentations, may be used inter alia therefore. There is also the possibility of performing in the course of the calibration stimulations for an optional automatic adaptation of the intensity of the stimulation current to anatomical and patient-individual conditions.

In the subsequent step S2, at least an optimization of the number of stimulations to be used in the stimulation procedure, the associated stimulation locations in the portion of brain tissue and the sequence in which the stimulations are performed takes place. In addition, the orientation of the stimulation electrode 5 used for the stimulation in the stimulation and/or the direction from which the stimulation electrode 5 is to be brought up to the respective stimulation location may also be optimized. The optimizing method is explained later with reference to FIGS. 4A and 4B. The result of the optimization is visually presented to the user, that is to say the treating surgeon, on the monitor 9, as is explained later by way of example with reference to FIG. 3.

In the stimulation sequence optimized in step S2, the stimulations later take place in such a way that subsequent stimulations in the series of the respective stimulations never influence the optical responses of the respectively activated brain tissue region caused by previous stimulations (for example by a cast shadow, coverages by stimulation electrodes, etc.). The anatomical regions segmented in the course of the calibration are, in this case, used in the course of the optimization S2 to avoid major vessels or sulci being located between the poles of a stimulation electrode.

Figure 3:
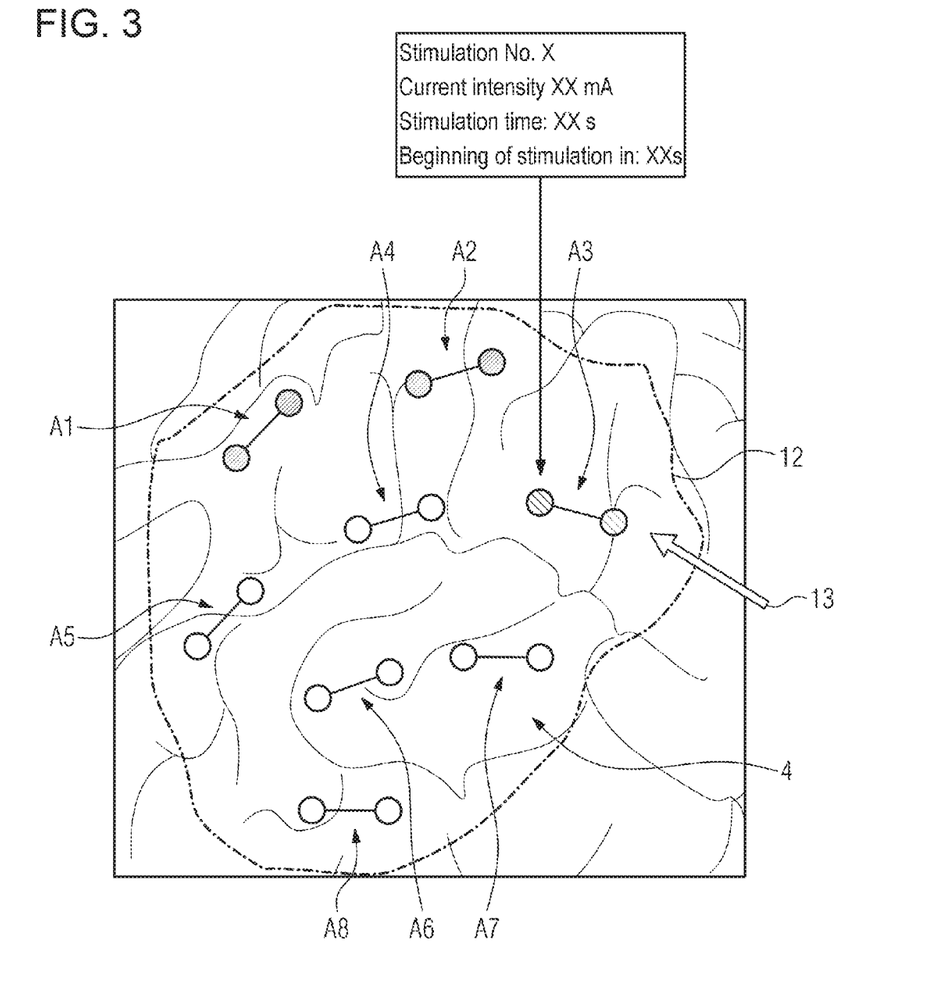
FIG. 3 shows a diagram in which the stimulation locations and the stimulation sequence in the stimulation of a portion of brain tissue are depicted.

FIG. 3 shows the exposed portion of brain tissue, which is marked by the boundary line 12. Within the boundary line 12, stimulation locations A1 to A8 are marked on the monitor, the numbering indicating the sequence in which individual stimulations are to be performed. The circles joined to one another by a line at the respective stimulation locations in this case indicate the placements of the poles 5A and 5B of the stimulation electrode 5—and consequently the orientation of the stimulation electrode 5 in the stimulation. In the present diagram, the stimulation locations A1 and A2, which are represented by circles filled with closely hatched lines, represent those stimulation locations that have already been stimulated. The stimulation location A3, at which the circles are filled with less closely hatched lines, represents the location at which the current stimulation is to be performed, and the stimulation locations A4 to A8, with the circles that are not filled, represent those stimulation locations that have not yet been stimulated the stimulation location currently to be stimulated. For the stimulation location currently to be stimulated, also indicated along with the number of the stimulation in the stimulation sequence are the intensity of the current with which the stimulation is to be performed, the stimulation time and the point in time at which the stimulation begins. In addition, a direction arrow 13 indicates from which direction the stimulation electrode 5 is to be applied in order to cause as little covering of brain tissue as possible by the applied stimulation electrode 5 and cause as little cast shadow as possible in the exposed portion of brain tissue 4.

Once the optimization has been performed in step S2, the recording of a video sequence of the exposed brain tissue region without a stimulation taking place takes place in step S3. This video sequence serves as a reference video sequence, which is subsequently compared with video sequences of the individual stimulations in order to make the brain tissue regions of the exposed portion of brain tissue 4 that are activated by the respective stimulation identifiable on the basis of the differences in the recorded video sequences found in the comparison. For locating the differences, in the present exemplary embodiment the intensities are compared in the green wavelength range. The stimulation leads to an increased perfusion of the activated brain tissue region, which in turn leads to an increased absorption in the green wavelength range. By forming the difference between the reference video sequence on the one hand and a video sequence recorded during and/or after a stimulation on the other hand, the locations of increased absorption in the portion of brain tissue can be made identifiable in the difference image as bright spots, which then identify the activated brain tissue region.

If then in step S4 a stimulation of the stimulation locations established in the course of the optimizing method is performed one after the other in the likewise established stimulation sequence, as it is represented in FIG. 3, the brain tissue regions of the exposed portion of brain tissue 4 that are respectively activated by the individual stimulations can be established on the basis of a comparison of the video sequence recorded during and/or after the respective stimulation with the reference video sequence. Since the activated brain tissue regions respectively represent functional brain tissue, the surgeon obtains an overview of where the functional brain tissue is located in the exposed portion of brain tissue 4.

Although in the present exemplary embodiment a dedicated video sequence for each stimulation is recorded during and/or after the respective stimulation, the method may also be performed in such a way that an overall video sequence which includes all of the stimulations is recorded. Forming the difference from the overall video sequence and the reference video sequence then has the effect that the activated brain tissue regions become visible one after the other in the resultant difference video sequence.

In particular, because in the course of the present method only a single reference video sequence has to be recorded, the time required for performing the stimulation procedure is shortened considerably. The described difference generation takes place in the method according to an aspect of the disclosure in the course of step S5, which represents the evaluation of the recorded video sequences.

The optimizing of the number of stimulations, the associated stimulation locations in the exposed portion of brain tissue 4 and the sequence of the electrical stimulations is described below with reference to FIGS. 4A and 4B, which shows a flow chart of the optimizing method.

Once the optimizing method has been started in step S201, a calculation of the areal extent to be expected of a brain tissue region activated by a stimulation takes place in step S202. The calculation takes place on the basis of an image which has been recorded for example in the course of the calibrating and data capturing steps performed in step S1 of the exposed portion of brain tissue 4 after a stimulation at a specific location of the portion of brain tissue 4, and which is compared with a reference image without stimulation that is, for example, likewise recorded in the course of the calibrating and data capturing steps performed in step S1. Typically, the image used for the calibration is recorded at a location of the exposed portion of tissue 4 at which the smallest areal extent of activated brain tissue region is to be expected. As a result, while accepting an overlap of the activated brain tissue regions, it can be prevented that parts of the exposed portion of tissue 4 are not checked with regard to activation by stimulation in the course of the stimulation procedure because of an overestimated areal extent.

On the basis of the (minimum) area of extent to be expected of an activated brain tissue region calculated in step S202, the required number of stimulations and the associated stimulation locations are calculated in step S204, while no allowance for anatomical conditions is made as yet in the choice of stimulation locations. For calculating the required number of stimulations, in the simplest case the overall area of the exposed portion of brain tissue 4 may be divided by the areal extent to be expected of an activated brain tissue region. At the end of the method, the number of stimulation locations ultimately required may be higher than the number obtained by the described division, since the final choice of stimulation locations must make allowance for anatomical conditions such as sulci or vessels. Thus, as far as possible, no sulci or major vessels should run between the poles 5A and 5B of the stimulation electrode 5. The optimization of the stimulation locations with regard to the anatomical conditions takes place in the present exemplary embodiment on the basis of the optimization routine described with respect to the method steps S205 to S215.

Step S205 marks the beginning of the optimization routine in which the position and orientation of the poles 5A and 5B of the stimulation electrode 5 are optimized for each stimulation location determined in step S204.

In step S206, the existence of a termination criterion which indicates that an optimization is not possible for one of the stimulation locations determined in step S204 is checked. For example, a prescribed number of unsuccessful optimization attempts for a stimulation location may serve as a termination criterion. If the termination criterion is satisfied, i.e. if in the stated example the prescribed number of unsuccessful optimization attempts is reached, the optimization routine is ended and the method returns to step S204, where the number of stimulations and the associated stimulation locations are calculated by using alternative parameters. For example, a smaller value for the areal extent of activated brain tissue region may be used in the recalculation, so that the recalculation leads to a higher number of stimulation locations.

If, on the other hand, it is established in step S206 that the termination criterion has not yet been satisfied, the method continues to step S207, in which the first stimulation location is selected in the first run and the next stimulation location is selected in the subsequent runs. For the selected stimulation location, it is then checked in step S208 whether the poles 5A and 5B of the stimulation electrode 5 are arranged on different sides of the vessel or of a sulcus. If this is the case, the method continues to step S209, in which the position of the stimulation electrode 5 and/or the orientation of the poles 5A and 5B of the stimulation electrode 5 is or are changed. In step S210, it is then determined whether the change performed in step S209 has the effect that the poles 5A and 5B of the stimulation electrode 5 are then no longer lying on different sides of a major vessel or of a sulcus. If this is affirmed, the method continues to step S211. Otherwise, the method returns to step S206, while indicating a termination criterion. In a variant of the optimization routine, the position of the stimulation electrode 5 and/or the orientation of the poles 5A and 5B of the stimulation electrode 5 is changed a number of times, and after each change it is determined whether the poles 5A and 5B of the stimulation electrode 5 are no longer lying on different sides of a major vessel or of a sulcus. Only if the poles 5A and 5B of the stimulation electrode 5 are still arranged on different sides of the vessel or of a sulcus after a prescribed number of changes of the position of the stimulation electrode 5 and/or the orientation of the poles 5A and 5B does the method return to step S206, while indicating the termination criterion. If on the other hand it is determined in step S208 that the poles 5A and 5B of the stimulation electrode 5 are not arranged on different sides of the vessel or of a sulcus, the method continues directly to step S211.

In step S211, a check takes place to determine whether the position of the stimulation electrode 5 found in the current optimization leads in the likewise found orientation of its poles 5A and 5B to an activated brain tissue region that overlaps with another activated brain tissue region. If this is the case, the method continues to step S212, in which the position of the electrode 5 and/or the orientation of its poles 5A and 5B is changed, in order to minimize or eliminate the overlap. If it is then determined in step S213 that the overlap has been minimized or eliminated, the method continues to step S214. Otherwise, the method returns to step S206, while indicating a termination criterion. Also in the optimization with regard to the overlap there is the possibility of changing the position of the stimulation electrode 5 and/or the orientation of the poles 5A and 5B of the stimulation electrode 5 a number of times and of checking after each change whether the overlap has been minimized or eliminated. Only if the overlap has still not been eliminated or sufficiently minimized after a prescribed number of changes of the position of the stimulation electrode 5 and/or the orientation of the poles 5A and 5B does the method return to step S206, while indicating the termination criterion. If on the other hand it is determined in step S211 that there is no overlap, the method continues directly to step S214.

In step S214, it is determined whether an optimization of the position of the stimulation electrode 5 and the orientation of the poles 5A and 5B has taken place for all of the stimulation locations determined in step S204. If this is the case, the method continues to step S215, in which the optimization routine is ended, before the method continues to step S216. Otherwise, the method returns to step S207, and the optimization routine performs the optimization of the position of the stimulation electrode 5 and the orientation of its poles 5A and 5B for the next stimulation location determined in step S204.

In step S216, finally, an optimization of the sequence with which the determined simulation locations are simulated, and also the direction from which the stimulation electrode 5 is brought up to the respective stimulation location, takes place. In this case, while making allowance for the direction of illumination and the direction of recording, the direction from which the stimulation electrode 5 is brought up to the respective stimulation location is optimized in such a way that as far as possible no covering of the brain tissue region activated by the stimulation takes place and the activated brain tissue region is also not obscured by shadow. When optimizing the stimulation sequence, the stimulation locations are temporally sorted in such a way that, while making allowance for the decay time of an activation of a brain tissue region caused by a stimulation, successive stimulation locations are spatially far apart from one another to such an extent that the brain tissue regions activated by the respective stimulation do not overlap one another and/or the stimulations at stimulation locations lying spatially close to one another in such a way that the brain tissue regions activated by the respective stimulation spatially overlap one another take place at a time interval of such a length that the activation resulting from the stimulation of one of the stimulation locations lying spatially close to one another has decayed when the stimulation of the other of the stimulation locations lying spatially close to one another takes place.

Once the sequence with which the stimulation locations are stimulated as well as the direction from which the stimulation electrode is brought up to the respective stimulation locations have been optimized, the method continues to step S217, in which it is determined whether a prescribed quality criterion for the determined sequence is satisfied. If this is the case, the optimizing method is ended in step S218, and the optimized number of stimulations, the associated stimulation locations and the sequence of the stimulations are output on the monitor 9, in order that the treating surgeon can carry out the stimulations in the specified sequence. Otherwise, the method returns to step S204, where the number of stimulations and the associated simulation locations are calculated by using alternative parameters. For example, a smaller value for the areal extent of activated brain tissue region may be used in the recalculation, so that the recalculation leads to a higher number of stimulation locations.

Figure 4A:
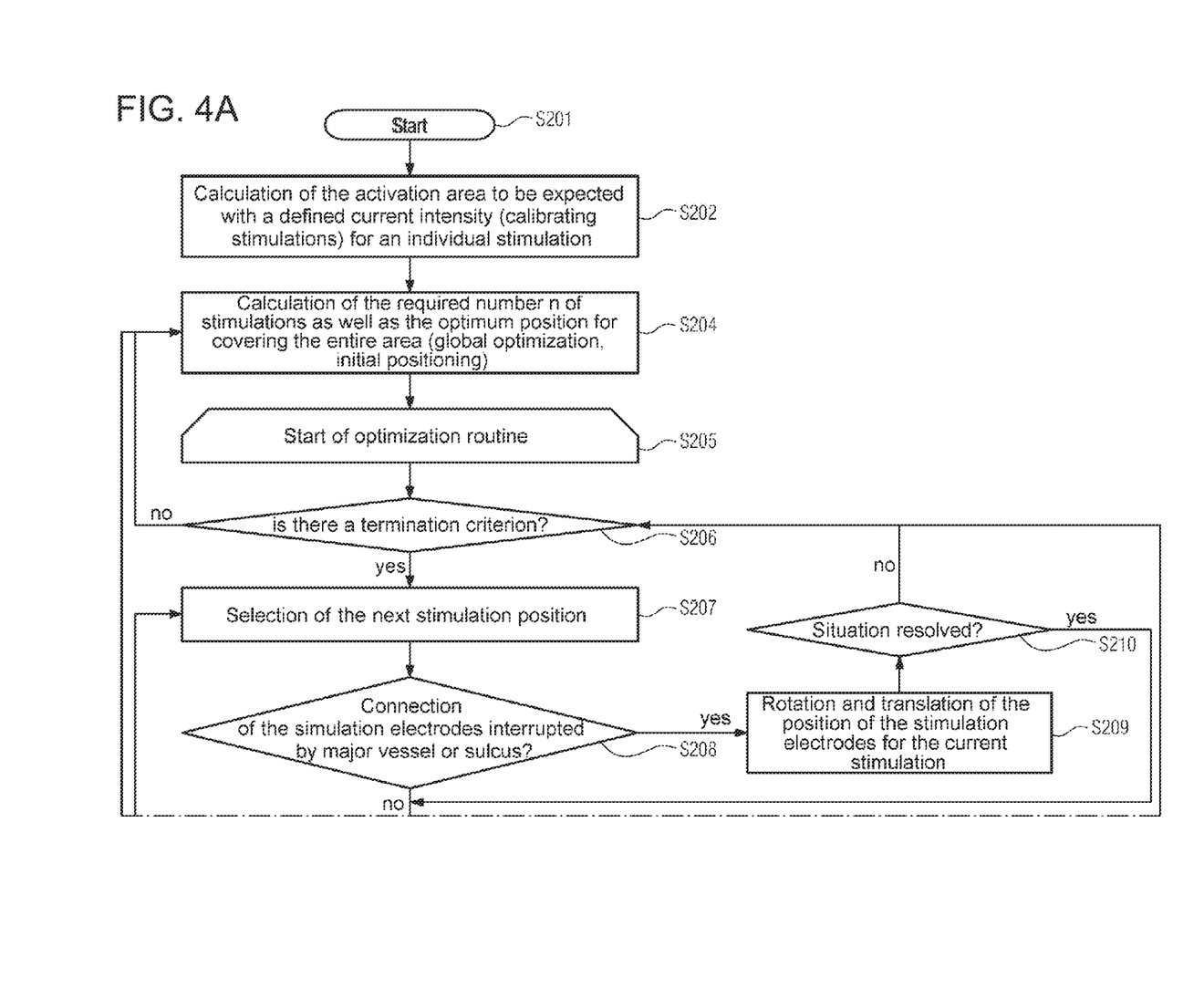
FIGS. 4A and 4B show a flow chart of a method for optimizing the number of stimulations, the associated stimulation locations, and the sequence of the stimulations.
Figure 4B:
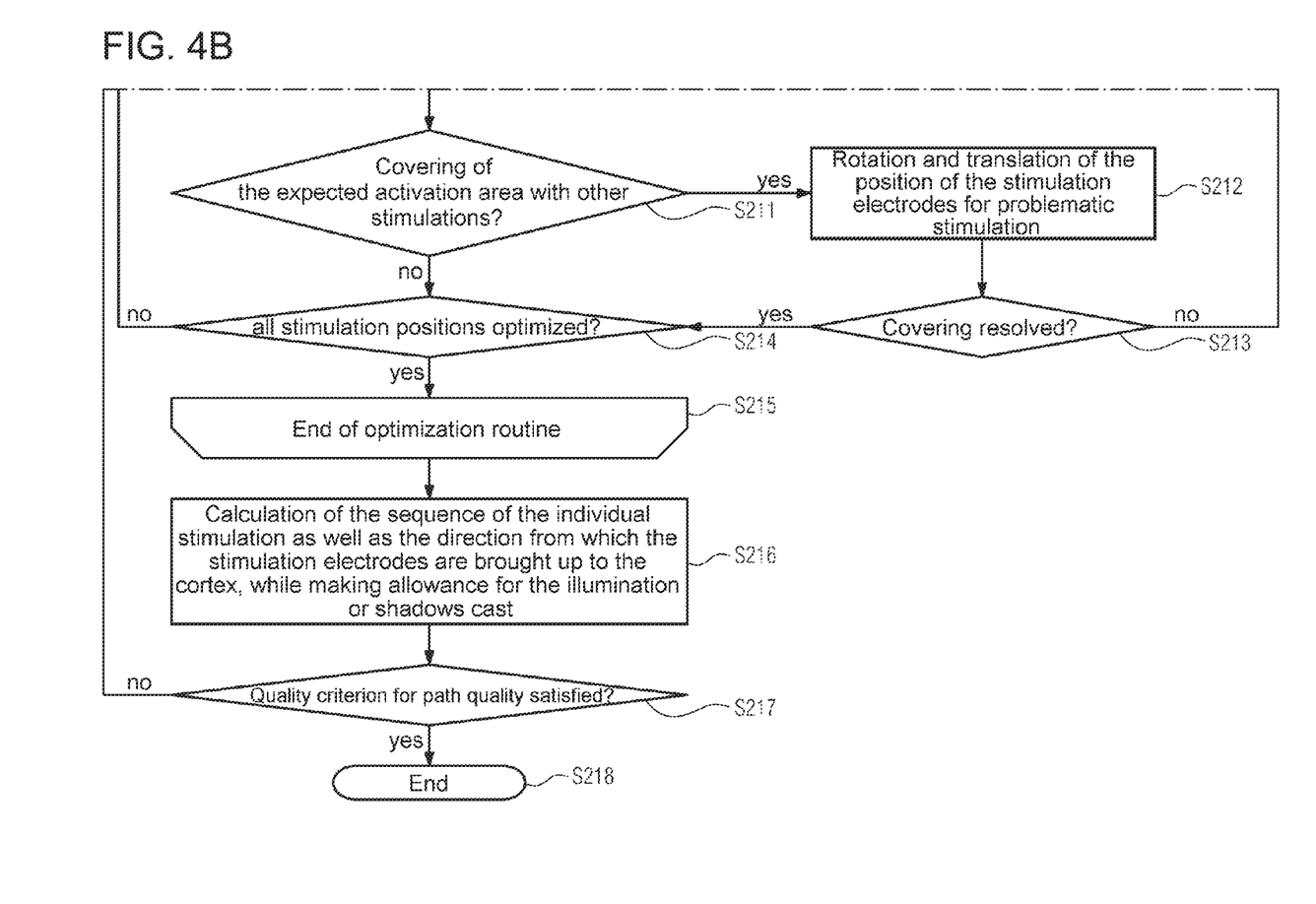

In the present exemplary embodiment, the optimizing method described with reference to FIGS. 4A and 4B is carried out, e.g., by a processor, on a computer 11. For this purpose, the method according to the disclosure may be in the form of instructions which are stored on a nonvolatile non-transitory computer-readable storage medium and which, when they are loaded onto and carried out by the computer, cause the computer to carry out the optimizing method.

The optimization performed with the optimizing method prevents that the activated brain tissue regions resulting from the stimulation of different stimulation locations overlap one another. As a result, there is the possibility that all of the activations are recorded in a single video sequence and this video sequence is compared with a single reference video sequence. To the contrary, in the prior art, a dedicated video sequence is recorded for each stimulation and is compared with a dedicated reference video sequence recorded before the respective stimulation. Therefore, the described optimization allows the time taken for the stimulation procedure to be shortened considerably in comparison with the prior art. In the course of the evaluation of the video sequences, the points in time of the stimulation are documented during the stimulation by the device or are calculated retrospectively from the video data or timestamps. For each stimulation location, an activation chart can then be separately calculated. The individual activation charts may then be subsequently joined together again in a way corresponding to the position of the stimulation locations to form an overall chart. As a result, at the end the user is presented with a visual diagram of the changing of the change in optical properties of the brain tissue due to the stimulation, synchronized for all of the stimulation locations.

The present disclosure has been described in detail on the basis of an exemplary embodiment for the purposes of explanation. However, a person skilled in the art will appreciate that it is possible to depart from the exemplary embodiment. For example, in the exemplary embodiment, the stimulations at different stimulation locations are carried out strictly one after the other. However, in principle there is also the possibility of carrying out stimulations simultaneously, if it is established in the optimizing method that the brain tissue regions activated by the respective stimulations do not spatially overlap one another, even if this would be difficult to perform in current surgical practice. For this purpose, the device represented in FIG. 1 may include a number of bipolar stimulation electrodes. Simultaneous stimulation at different stimulation locations allows the time required for the stimulation procedure to be reduced further. In addition, the optimizing method has further optimization criteria. For example, it is not only possible to vary the location of the stimulation electrode and the orientation of its poles in the course of the optimization, but also to consider the use of a stimulation electrode with a different form of electrode. Therefore, the present disclosure is not intended to be restricted to the configurational variant described, but rather only by the appended claims.

In other words, it is understood that the foregoing description is that of the exemplary embodiments of the disclosure and that various changes and modifications may be made thereto without departing from the spirit and scope of the disclosure as defined in the appended claims.

What is claimed is:

1. A method for locating a functional brain tissue of a portion of brain tissue by electrical stimulation, the method comprising:
    performing a plurality of electrical stimulations of different areas of the portion of brain tissue to activate brain tissue regions of the portion of brain tissue, an activated brain tissue region of the portion of brain tissue identifying the functional brain tissue of the portion of brain tissue;
    recording at least one image or a video sequence of the portion of brain tissue during and/or after at least one of the plurality of electrical stimulations;
    comparing the at least one image recorded during and/or after the at least one of the plurality of stimulations or the video sequence recorded during and/or after the at least one of the plurality of electrical stimulations with a reference image or a reference video sequence of the portion of brain tissue without the at least one of the plurality of electrical stimulations to determine a position of at least one brain tissue region in the portion of brain tissue that is activated by the at least one of the plurality of electrical stimulations;
    wherein at least two of the plurality of electrical stimulations are performed directly one after another or simultaneously, and
    wherein the at least one image or the video sequence of the portion of brain tissue is/are recorded during and/or after each of the at least two of the plurality of electrical stimulations, respectively, or during and/or after simultaneously performing of the at least two of the plurality of electrical stimulations.

2. The method as claimed in claim 1, wherein:
    the reference image or the reference video sequence of the portion of brain tissue without the at least one of the plurality of electrical stimulations is only a single reference image or a single reference video sequence of the portion of brain tissue, and
    the single reference image or the single reference video sequence is recorded before performing the plurality of electrical stimulations of the different areas of the portion of brain tissue.

3. The method as claimed in claim 2, further comprising:
    comparing the at least one image recorded during and/or after the at least one of the plurality of electrical stimulations or of the video sequence recorded during and/or after the at least one of the plurality of stimulations with the single reference image or the single reference video sequence.

4. The method as claimed in claim 1, further comprising:
    optimizing the plurality of electrical stimulations, stimulation locations in the portion of brain tissue, and a sequence of the plurality of electrical stimulations such that the brain tissue regions activated by the plurality of electrical stimulations do not spatially overlap one another and/or activations of the brain tissue regions caused by the plurality of electrical stimulations and spatially overlapping one another do not temporally overlap.

5. The method as claimed in claim 4, wherein the optimizing comprises:
    determining an areal extent of a stimulation-activated brain tissue region to be expected during an electrical stimulation of an area of the portion of brain tissue;
    determining the plurality of electrical stimulations required for covering an overall area of the portion of brain tissue and the stimulation locations from the overall area of the portion of brain tissue and the areal extent to be expected of the stimulation-activated brain tissue region; and
    establishing the sequence of the plurality of electrical stimulations with the stimulation locations in the portion of brain tissue while allowing a decay time of an activation of a brain tissue region caused by the electrical stimulation for a determined number of electrical stimulations such that successive stimulation locations are spatially far apart from one another to such an extent that the brain tissue regions activated by the plurality of electrical stimulations do not overlap one another and/or the plurality of electrical stimulations at the stimulation locations lying spatially close to one another such that the brain tissue regions activated by the at least one of the plurality of electrical stimulations spatially overlap one another at a time interval of a length that the activation resulting from the at least one of the plurality of stimulations of one of the stimulation locations lying spatially close to one another has decayed when the stimulation of the other of the stimulation locations lying spatially close to one another is performed.

6. The method as claimed in claim 5, further comprising:
    determining the areal extent of the activated brain tissue region to be expected when performing the at least one of the plurality of electrical stimulations of the area of the portion of brain tissue based on a calibration image recorded during and/or after performing the at least one of the plurality of electrical stimulations or a calibration video sequence recorded during and/or after performing the at least one of the plurality of electrical stimulations.

7. The method as claimed in claim 4, further comprising:
optimizing a position and/or an orientation of an electrode at which the at least one of the plurality of electrical stimulations is performed based on a direction of illumination such that coverings of the activated brain tissue region caused by the electrode in the at least one image recorded during and/or after the performing of the at least one of the plurality of electrical stimulations or in the video sequence recorded during and/or after performing the at least one of the plurality of electrical stimulations, are minimized.

8. The method as claimed in claim 4, further comprising: considering maximum distances between the stimulation locations and/or increased minimum distances between stimulation locations of successive stimulations.

9. The method as claimed in claim 4, further comprising:
optimizing a position and/or an orientation of an electrode at which the at least one of the plurality of electrical stimulations is performed based on a direction of illumination such that cast shadows in the portion of the brain tissue caused by the electrode in the at least one image recorded during and/or after the performing of the at least one of the plurality of electrical stimulations or in the video sequence recorded during and/or after performing at least one of the plurality of stimulations, are minimized.

10. The method as claimed claim 4, further comprising:
re-optimizing a remaining portion of the plurality of electrical stimulations after performing an initial portion of the plurality of electrical stimulations, the stimulation locations in the portion of the brain tissue, and the sequence of the at least one of the plurality of electrical stimulations.

11. The method as claimed in claim 1, further comprising:
recording a single video sequence which includes each of the plurality of electrical stimulations of different areas of the portion of the brain tissue to record the at least one image or the video sequence of the portion of brain tissue during and/or after the performing of the plurality of electrical stimulations.

12. A computer-implemented method for optimizing a plurality of electrical stimulations, stimulation locations, and a stimulation sequence when performing a plurality of electrical stimulations of different areas of a portion of a brain tissue for activating brain tissue regions of the portion of the brain tissue, the method comprising:
determining an areal extent of a stimulation-activated brain tissue region to be expected during an electrical stimulation of an area of the portion of the brain tissue;
determining the plurality of electrical stimulations required for covering an overall area of the portion of the brain tissue and the stimulation locations from the overall area of the portion of the brain tissue and the areal extent to be expected of an activated brain tissue region; and
establishing a sequence of the plurality of electrical stimulations with the stimulation locations in the portion of brain tissue while allowing a decay time of an activation of a brain tissue region caused by the electrical stimulation for a determined number of stimulations such that successive stimulation locations are spatially far apart from one another to such an extent that the brain tissue regions activated by the plurality of electrical stimulations do not overlap one another and/ or the plurality of electrical stimulations at the stimulation locations lying spatially close to one another such that the brain tissue regions activated by the at least one of the plurality of electrical stimulations spatially overlap one another at a time interval of a length that the activation resulting from the at least one of the plurality of electrical stimulations of one of the stimulation locations lying spatially close to one another has decayed when the stimulation of the other of the stimulation locations lying spatially close to one another is performed.

13. The computer-implemented method as claimed in claim 12, further comprising:
determining the areal extent of the activated brain tissue region to be expected when performing the at least one of the plurality of electrical stimulations of the area of the portion of the brain tissue based on a calibration image recorded during and/or after performing the at least one of the plurality of electrical stimulations or a calibration video sequence recorded during and/or after performing of the at least one of the plurality of electrical stimulations.

14. The computer-implemented method as claimed in claim 12, further comprising:
optimizing a position and/or an orientation of an electrode at which the at least one of the plurality of electrical stimulations is performed based on a direction of illumination such that coverings of the activated brain tissue region caused by the electrode in at least one image recorded during and/or after performing the at least one of the plurality of electrical stimulations or in a video sequence recorded during and/or after performing the at least one of the plurality of electrical stimulations, are minimized.

15. The computer-implemented method as claimed in claim 12, further comprising:
optimizing a position and/or an orientation of an electrode at which the at least one of the plurality of electrical stimulations is performed based on a direction of illumination such that cast shadows caused by the electrode in at least one image recorded during and/or after performing the at least one of the plurality of stimulations or in a video sequence recorded during and/or after the performing of the at least one of the plurality of stimulations, are minimized.

16. A non-transitory computer-readable storage medium with instructions stored thereon for optimizing a plurality of electrical stimulations, stimulation locations, and a stimulation sequence when performing a plurality of electrical stimulations of different areas of a portion of a-brain tissue for activating brain tissue regions of the portion of the brain tissue, the instructions, when carried out on a computer, causing the computer to:
determine an areal extent of a stimulation-activated brain tissue region to be expected in during an electrical stimulation of an area of the portion of brain tissue;
determine the plurality of electrical stimulations required for covering an overall area of the portion of brain tissue and the stimulation locations from the overall area of the portion of the brain tissue and the areal extent to be expected of the stimulation-activated brain tissue region; and
establish a sequence of the plurality of electrical stimulations with the stimulation locations in the portion of brain tissue while allowing a decay time of an activation of a brain tissue region caused by the electrical stimulation for a determined number of electrical stimulations such that successive stimulation locations are spatially far apart from one another to such an extent that the brain tissue regions activated by the plurality of electrical stimulations do not overlap one another and/or the plurality of electrical stimulations at the stimulation locations lying spatially close to one another such that the brain tissue regions activated by the at least one of the plurality of electrical stimulations spatially overlap one another at a time interval of a length that the activation resulting from the at least one of the plurality of stimulations of one of the stimulation locations lying spatially close to one another has decayed when the stimulation of the other of the stimulation locations lying spatially close to one another is performed.

17. An apparatus for locating a functional brain tissue of a portion of a brain tissue by a plurality of electrical stimulations, the apparatus comprising:

at least one bipolar stimulation electrode configured to stimulate areas of the portion of the brain tissue to activate brain tissue regions of the portion of the brain tissue, wherein an activated brain tissue region of the portion of the brain tissue identifies the functional brain tissue of the portion of the brain tissue;

at least one camera to record at least one reference image or a reference video sequence of the portion of the brain tissue without stimulation and at least one image or a video sequence of the portion of the brain tissue during and/or after at least one of the plurality of electrical stimulations;

an evaluation device configured to determine a position of at least one brain tissue region in the portion of the brain tissue that is activated during the at least one of the plurality of electrical stimulations based on a comparison of the image recorded during and/or after the at least one of the plurality of stimulations or the video sequence recorded during and/or after the at least one of the plurality of stimulations with the at least one reference image or the reference video sequence of the portion of the brain tissue recorded without the stimulation; and an optimization device configured to optimize the plurality of electrical stimulations, associated stimulation locations, and a sequence of the plurality of electrical stimulations.

* * * * *

UNITED STATES PATENT AND TRADEMARK OFFICE
CERTIFICATE OF CORRECTION

PATENT NO. : 10,993,620 B2
APPLICATION NO. : 16/586972
DATED : May 4, 2021
INVENTOR(S) : Tobias Meyer et al.

It is certified that error appears in the above-identified patent and that said Letters Patent is hereby corrected as shown below:

In the Claims

In Column 17:
Line 40: Delete "of the portion of the brain tissue to record the at least" and insert -- of the portion of brain tissue to record the at least -- therefor.

In Column 18:
Line 21: Delete "performing of the at least one of the plurality of" and insert -- performing the at least one of the plurality of -- therefor.

In Column 18:
Line 50: Delete "stimulations of different areas of a portion of a-brain tissue" and insert -- stimulations of different areas of a portion of brain tissue -- therefor.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*